United States Patent
Shirley et al.

(10) Patent No.: US 7,262,168 B2
(45) Date of Patent: *Aug. 28, 2007

(54) COMPOSITIONS PROVIDING FOR INCREASED IGF-I SOLUBILITY

(75) Inventors: Bret A. Shirley, Waltham, MA (US); Kamaljit Bajwa, Danville, CA (US)

(73) Assignee: Chiron Corporation, Emeryville, CA (US)

(*) Notice: Subject to any disclaimer, the term of this patent is extended or adjusted under 35 U.S.C. 154(b) by 143 days.

This patent is subject to a terminal disclaimer.

(21) Appl. No.: 11/230,105

(22) Filed: Sep. 19, 2005

(65) Prior Publication Data

US 2006/0074011 A1    Apr. 6, 2006

Related U.S. Application Data

(60) Continuation of application No. 10/843,034, filed on May 11, 2004, now Pat. No. 6,951,842, which is a division of application No. 09/188,051, filed on Nov. 6, 1998, now Pat. No. 6,767,892.

(60) Provisional application No. 60/064,891, filed on Nov. 7, 1997.

(51) Int. Cl.
*A61K 38/30* (2006.01)
*C07K 14/00* (2006.01)

(52) U.S. Cl. .................. 514/12; 514/634; 530/300; 530/324; 530/303; 530/399

(58) Field of Classification Search .................. 514/12, 514/634; 530/300, 324, 303, 399
See application file for complete search history.

(56) References Cited

U.S. PATENT DOCUMENTS

| | | | |
|---|---|---|---|
| 4,769,361 A | 9/1988 | Burleigh et al. | |
| 5,126,324 A | 6/1992 | Clark et al. | |
| 5,231,178 A | 7/1993 | Holtz et al. | |
| 5,352,452 A | 10/1994 | Kohnert et al. | |
| 5,410,026 A | 4/1995 | Chang et al. | |
| 5,597,897 A | 1/1997 | Ron et al. | |
| 5,681,814 A | 10/1997 | Clark et al. | |
| 6,767,892 B1 * | 7/2004 | Shirley et al. | 514/12 |

FOREIGN PATENT DOCUMENTS

| | | |
|---|---|---|
| EP | 0 217 379 | 4/1987 |
| WO | WO92/04363 | 3/1992 |
| WO | WO94/15584 | 7/1994 |

OTHER PUBLICATIONS

Fransson, et al., "Local Tolerance of Subcutaneous Injections" *Journal of Pharm. Pharmacol.* (1996) pp. 1012-1015, vol. 48.
The Merck Index, 12th ed., Merck & Co., Inc., Whitehouse Station, NJ, 1996, p. 7724.

* cited by examiner

*Primary Examiner*—Chih-Min Kam
(74) *Attorney, Agent, or Firm*—Leslie T. Henry; Susan Abrahamson; Alisa A. Harbin

(57) ABSTRACT

Novel IGF-I compositions are described. The compositions include a solubilizing compound comprising a guanidinium group that provides for IGF-I compositions in which IGF-I is highly soluble at pHs of about 5.5 or greater and at refrigerated temperatures.

19 Claims, 5 Drawing Sheets

COMPOSITIONS PROVIDING FOR INCREASED IGF-I SOLUBILITY

CROSS-REFERENCE TO RELATED APPLICATIONS

This application is a continuation of U.S. patent application Ser. No. 10/843,034, filed May 11, 2004, now U.S. Pat. No. 6,951,842, which is a divisional of U.S. patent application Ser. No. 09/188,051, filed Nov. 6, 1998, now U.S. Pat. No. 6,767,892, which claims the benefit of U.S. Provisional Application No. 60/064,891, filed Nov. 7, 1997, the contents of which are herein incorporated by reference in their entirety.

FIELD OF THE INVENTION

The present invention relates generally to pharmaceutical compositions. More particularly, the invention relates to IGF-I compositions that provide high concentrations of soluble IGF-I at desirable pHs.

BACKGROUND OF THE INVENTION

Insulin-like growth factor-I (IGF-I) belongs to a family of polypeptides known as somatomedins. IGF-I is structurally and functionally similar to, but antigenically distinct from, insulin. In this regard, IGF-I is a single-chain polypeptide with three intrachain disulfide bridges and four domains known as the A, B, C, and D domains, respectively. The A and B domains are connected by the C domain and are homologous to the corresponding domains of proinsulin. The D domain, a carboxy terminal extension, is present in IGF-I but is absent from proinsulin. IGF-I has 70 amino acid residues and a molecular mass of approximately 7.5 kDa (see Rinderknecht, *J Biol. Chem.* (1978) 253:2769; and Rinderknecht, *FEBS Lett.* (1978) 89:283). For a review of IGF, see Humbel, *Eur. J Biochem.* (1990) 190:445–462.

IGF-I stimulates growth and division of a variety of cell types, particularly during development. See, e.g., EP 560, 723 A and 436,469 B. Thus, processes such as skeletal growth and cell replication are affected by IGF-I levels.

Due to the widely varied clinical applications for IGF-I, compositions with desirable characteristics are in great demand and several IGF-I formulations have been made. See, e.g., U.S. Pat. No. 5,126,324. In particular, compositions with high concentrations of IGF-I are preferable for certain indications. Additionally, it is preferable to administer IGF-I compositions at physiological pHs. It is also preferable that the IGF-I in such compositions remain soluble and that the compositions are capable of storage for extended periods of time at refrigerated temperatures.

Physical parameters such as temperature and pH affect the solubility of IGF-I. For example, below about pH 5.0, IGF-I is soluble at concentrations of about 80–100 mg/ml while above pH 5.5, the solubility drops about ten-fold. Additionally, IGF-I is less soluble at lower temperatures. Thus, in order to provide IGF-I compositions capable of refrigerated storage, e.g., to retain stability, while still maintaining acceptable IGF-I solubility levels, compositions are now generally kept at a pH less than 5.0. Unfortunately, administration of IGF-I compositions at such nonphysiological pHs causes pain and irritation at the site of injection.

In order to overcome this problem, experimenters have attempted to formulate IGF-I in various buffers. For example, Fransson and Espander-Jansson, *J Pharm. Pharmacol.* (1996) 48:1012–1015, describe IGF-I compositions including 5 mg/ml IGF-I in isotonic saline, with phosphate buffer concentrations ranging from 5 to 50 mM, at pH 6.0–7.0. The authors found that pH 7.0 IGF-I preparations caused less pain than pH 6.0 preparations and that lower buffer strengths reduced pain at nonphysiological pHs. However, the authors concluded that IGF-I pH 7.0 preparations were not feasible due to the instability of IGF-I at this pH. International Publication No. WO 94/15584 describes isotonic IGF-I solutions at pH 5.5 to 6.5 with phosphate buffer present in an amount less than 50 mmol/L, which are reported to result in reduced pain upon injection.

Additionally, in order to avoid stability problems and prolong shelf life, protein formulations such as those including IGF-I are often provided in a freeze-dried form. See, e.g., U.S. Pat. No. 5,210,074, which describes dried IGF-I compositions that include a strong acid, such as hydrochloric acid, to increase the shelf life of the formulation. However, freeze-dried formulations require reconstitution prior to injection, which is inconvenient and can lead to dilution errors. Additionally, freeze drying is costly and time consuming. Thus, it would be advantageous to prepare IGF-I compositions with increased IGF-I solubility at pHs greater than pH 5.0 and at refrigerated temperatures.

SUMMARY OF THE INVENTION

Accordingly, the present invention provides for IGF-I compositions in which IGF-I is highly soluble at pHs of about 5.5 or greater and at refrigerated temperatures. In the inventive compositions described herein, IGF-I is present at higher concentrations at higher pHs than previously possible. Therefore, smaller volumes of IGF-I at pHs above 5.5 may be delivered to a subject with reduced pain.

Accordingly, in one embodiment, the invention relates to a composition comprising:
  (a) an IGF-I or an IGF-I analogue, wherein the IGF-I or IGF-I analogue is soluble in said composition at a concentration of at least about 12 mg/ml when said composition is at a temperature of about 4° C.; and
  (b) a solubilizing compound comprising a guanidinium group, wherein the composition has a pH of at least about pH 5.5.

In another embodiment, the subject invention is directed to a composition comprising:
  (a) an IGF-I or an IGF-I analogue, wherein the IGF-I or IGF-I analogue is soluble in said composition at a concentration of at least about 12 mg/ml when the composition is at a temperature of about 4° C.;
  (b) a solubilizing compound selected from the group consisting of arginine, an arginine analogue, and guanidine hydrochloride; and
  (c) a buffer such that the composition has a pH of about pH 5.5 to about pH 9.0.

In another embodiment, the subject invention is directed to a method of making an IGF-I composition comprising:
  (a) providing an amount of an IGF-I or an IGF-I analogue such that the IGF-I or IGF-I analogue is soluble in said composition at a concentration of at least about 12 mg/ml when the composition is at a temperature of about 4° C.; and
  (b) combining the IGF-I or IGF-I analogue with a solubilizing compound comprising a guanidinium group, wherein the pH of the composition is about pH 5.5 to about pH 9.0.

In yet a further embodiment, the invention is directed to a method of delivering an IGF-I composition to a vertebrate subject comprising:

(a) providing a composition as described above; and
(b) administering the IGF-I composition to the vertebrate subject.

In another embodiment, the invention is directed to a method of enhancing the solubility of IGF-I or an IGF-I analogue in a composition having a pH of from about pH 5.5 to about 9.0. The method comprises combining IGF-I or an IGF-I analogue with an amount of a solubilizing compound that comprises a guanidinium group sufficient to increase the solubility of IGF-I or the IGF-I analogue relative to the solubility of IGF-I or the IGF-I analogue in the absence of the solubilizing compound.

These and other embodiments of the subject invention will readily occur to those of skill in the art in light of the disclosure herein.

DETAILED DESCRIPTION OF THE INVENTION

Figure 1:
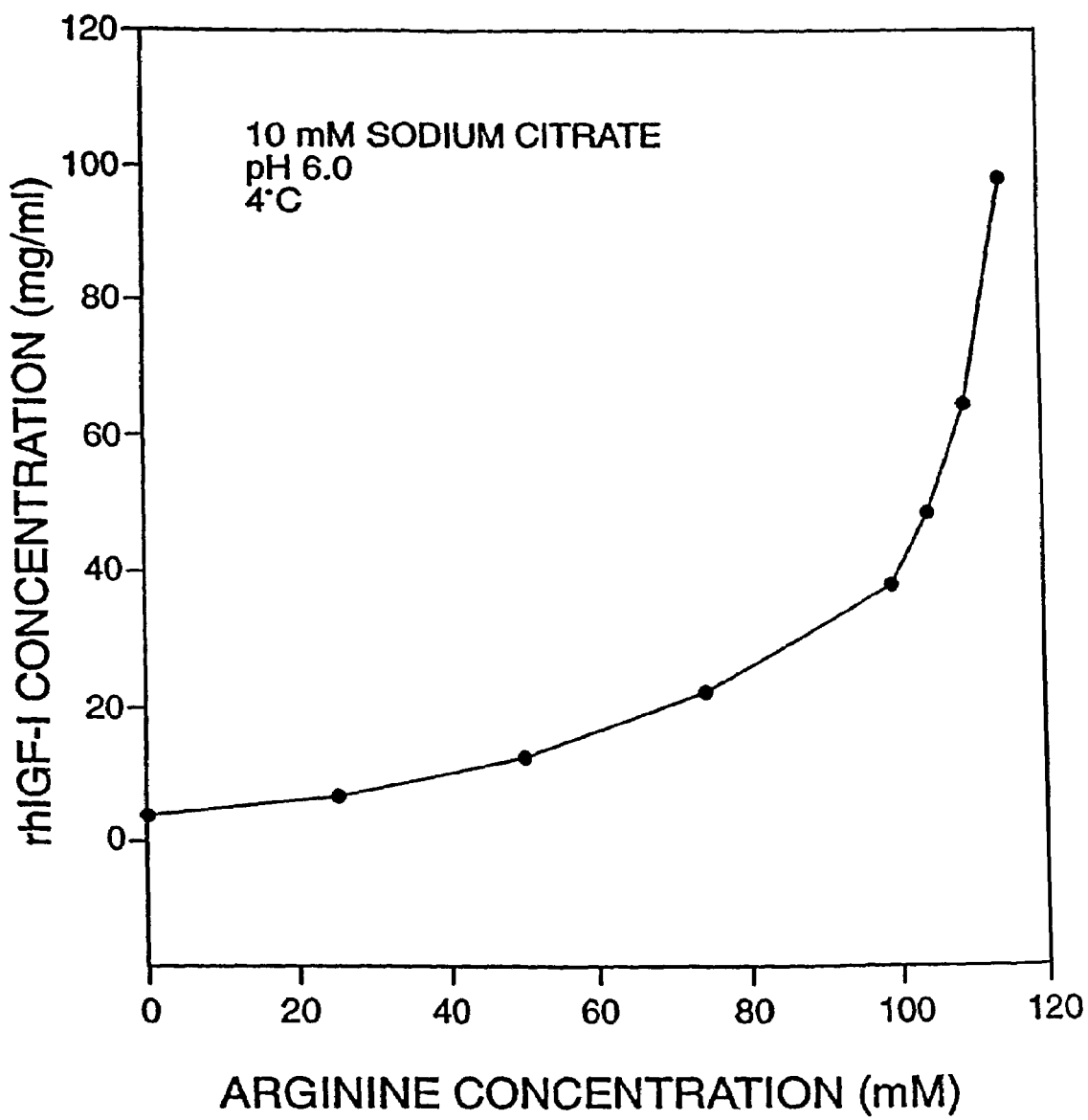
FIG. 1 shows recombinant human IGF-I ("rhIGF-I") solubility as a function of arginine concentration in a 10 mM sodium citrate buffer, pH 6.0, at 4° C.

The practice of the present invention will employ, unless otherwise indicated, conventional methods of protein chemistry, biochemistry, recombinant DNA techniques, and pharmacology, within the skill of the art. Such techniques are explained fully in the literature. See, e.g., Creighton, *Proteins: Structures and Molecular Properties* (W. H. Freeman and Company, New York, 1993); Lehninger, *Biochemistry* (Worth Publishers, Inc., New York, 1975); Sambrook et al., *Molecular Cloning: A Laboratory Manual* (2d ed., Cold Spring Harbor Laboratory Press, Plainview, N.Y., 1989); and Colowick and Kaplan, eds., *Methods in Enzymology* (Academic Press, New York).

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed and are intended to be defined as indicated below.

The term "insulin-like growth factor-I" or "IGF-I" as used herein refers to a compound having the primary, secondary, and/or tertiary molecular structure of native IGF-I and which has at least one IGF-I activity including activity as measured in standard IGF-I bioassays and/or the ability to bind IGF receptors. The IGF-I molecule may include posttranslational modifications, such as glycosylation, acetylation, phosphorylation, etc. Furthermore, for purposes of the present invention, an IGF-I compound may be derived from any of several tissues of any mammalian source, such as human, bovine, canine, equine, ovine, porcine, etc. The IGF-I compound may be purified directly from the source organism or may be recombinantly or synthetically produced (see further below).

The term "IGF-I analogue" refers to biologically active derivatives or fragments of IGF-I that retain IGF-I activity and/or the ability to bind IGF receptors. Such compounds may include amino acid additions, substitutions (generally conservative in nature), and deletions, relative to the native molecule, so long as the modifications do not destroy IGF-I activity including activity as measured in standard IGF-I bioassays and/or the ability of the molecule to bind to IGF receptors. Representative assays include known radioreceptor assays using placental membranes (see, e.g., U.S. Pat. No. 5,324,639; Hall et al., *J Clin. Endocrinol. and Metab.* (1974) 39:973–976; and Marshall et al., *J Clin. Endocrinol. and Metab.* (1974) 39:283–292), a bioassay that measures the ability of the molecule to enhance incorporation of tritiated thymidine, in a dose-dependent manner, into the DNA of BALB/c 3T3 fibroblasts (see, e.g., Tamura et al., *J Biol. Chem.* (1989) 262:5616–5621), and the like. Preferably, the analogue has at least the same activity as the native molecule.

IGF-I analogues will generally have at least 60%, preferably 70%, more preferably 80%, preferably 90% to 95% or more, and most preferably 98% or more, amino acid sequence identity to the amino acid sequence of the reference IGF-I molecule.

An analogue may differ by as few as 10, as few as 5, as few as 4, 3, 2, or even 1 amino acid residue. By "sequence identity" is intended the same amino acid residues are found within the IGF-I variant and the reference IGF-I molecule when a specified, contiguous segment of the amino acid sequence of the variant is aligned and compared to the amino acid sequence of the reference molecule. Methods for determining identity between sequences are well known in the art. See, for example, the ALIGN program (Dayhoff, in *Atlas of Protein Sequence and Structure* 5:Suppl. 3 (National Biomedical Research Foundation, Washington, D.C., 1978)) and programs in the Wisconsin Sequence Analysis Package, Version 8 (available from Genetics Computer Group, Madison, Wis.), for example, the GAP program. For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous nucleotides, and may be 30, 40, 50, 100, or more nucleotides. Corrections for increased sequence identity associated with inclusion of gaps in the variant's amino acid sequence can be made by assigning gap penalties. Methods of sequence alignment are well known in the art.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Meyers and Miller, *Computer Applic. Biol. Sci.* (1988) 4:11–17.

The art provides substantial guidance regarding the preparation and use of such IGF-I analogues, as discussed further below. A fragment of IGF-I will generally include at least about 10 contiguous amino acid residues of the full-length molecule, preferably about 15–25 contiguous amino acid residues of the full-length molecule, and most preferably about 20–50 or more contiguous amino acid residues of full-length IGF-I. The term "IGF-I analogue" also captures peptides having one or more peptide mimics ("peptoids"), such as those described in International Publication No. WO 91/04282.

Several IGF-I analogues and fragments are known in the art and include those described in, e.g., *Proc. Natl. Acad. Sci. USA* (1986) 83:4904–4907; *Biochem. Biophys. Res. Commun.* (1987) 149:398–404; *J Biol. Chem.* (1988) 263:6233–6239; *Biochem. Biophys. Res. Commun.* (1989) 165:766–771; Forsberg et al., *Biochem. J* (1990) 271:357–363; U.S. Pat. Nos. 4,876,242 and 5,077,276; International Publication Nos. WO 87/01038 and WO 89/05822. Representative analogues include one with a deletion of Glu-3 of the mature molecule, analogues with up to five amino acids truncated from the N-terminus, an analogue with a truncation of the first three N-terminal amino acids, and an analogue including the first 17 amino acids of the B chain of human insulin in place of the first 16 amino acids of human IGF-I.

The term "solubilizing compound" as used herein refers to a compound that includes a guanidinium group and which is capable of enhancing the solubility of IGF-I or an IGF-I analogue, as defined below. Examples of such solubilizing compounds include the amino acid arginine, as well as amino acid analogues of arginine that retain the ability to enhance solubility of IGF-I at pH 5.5 or greater. Such analogues include, without limitation, dipeptides and tripeptides that contain arginine. Other solubilizing compounds for use in the present compositions include any of the various guanidine compounds described further below.

By "enhancing the solubility" of IGF-I is meant increasing the amount of IGF-I that can be dissolved in solution at pH 5.5 or greater in the presence of a guanidinium-containing compound compared to the amount of IGF-I that can be dissolved at pH 5.5 or greater in a solution with the same components but lacking the guanidinium-containing compound. The ability of a guanidinium-containing compound to enhance the solubility of IGF-I can be determined using methods well known in the art.

For example, IGF-I solubility may be determined using a concentrated or saturated IGF-I solution, e.g., 50–200 mg/ml, pH 4.0, and dialyzing the IGF-I solution against a buffer solution, pH 5.5 or greater, with and without the solubilizing compound in question. After buffer exchange is complete, IGF-I will form two distinct phases, a layer of insoluble (precipitated) IGF-I and a solution phase containing a saturated solution of IGF-I. A sample of the solution phase is filtered to remove any insoluble material, and the concentration of the solution is determined by UV spectroscopy using the known IGF-I absorption coefficient, i.e., 0.62 absorbance units at 277 nm for a 1 mg/ml solution.

The quantity of IGF-I that can be dissolved in a given solvent to produce a saturated solution can also be determined visually by adding incremental amounts of IGF-I to the solvent until the IGF-I fails to dissolve completely. This can be done with and without the solubilizing compound in question. Solubility of IGF-I or an IGF-I analogue, of course, depends upon the environment and the particular IGF-I in question. Many parameters affect polypeptide solubility, including the temperature, the electrolyte environment, and the nature of the solvent.

"Pharmaceutically or therapeutically effective dose or amount" refers to a nontoxic dosage level sufficient to induce a desired biological result. That result can be reduction and/or alleviation of the signs, symptoms, or causes of a disease, or any other desired alteration of a biological system. Such amounts are described below.

By "vertebrate subject" is meant any member of the subphylum cordata, including, without limitation, humans and other primates, including nonhuman primates such as chimpanzees and other apes and monkey species; farm animals such as cattle, sheep, pigs, goats, and horses; domestic mammals such as dogs and cats; laboratory animals, including rodents such as mice, rats, and guinea pigs; birds, including domestic, wild, and game birds such as chickens, turkeys and other gallinaceous birds, ducks, geese, and the like. The term does not denote a particular age. Thus, both adult and newborn individuals are intended to be covered.

II. Modes of Carrying Out the Invention

The present invention is based on the discovery that guanidinium-containing compounds are able to enhance the solubility of IGF-I above pH 5.5, thereby providing for stable IGF-I compositions with higher concentrations of IGF-I than previously possible. The compositions of the present invention can also advantageously be stored at refrigerated temperatures for prolonged periods of time, e.g., for at least 6 months, and still maintain adequate solubility levels. The ability to refrigerate compositions in which IGF-I remains highly soluble prolongs the activity of the IGF-I. Additionally, the composition can be kept at a pH that is more desirable for administration in order to avoid pain.

As FIG. 1 shows, in the absence of a guanidinium-containing compound, IGF-I at pH 6.0 is only soluble to 3–4 mg/ml at 4° C. Furthermore, as shown in Table 1 below, IGF-I solubility at pH 6.0 is also greatly reduced at 4° C. as compared to solubility at room temperature. Thus, the addition of a solubilizing compound having a guanidinium group to an IGF-I composition provides for enhanced solubility, even at low temperatures. Accordingly, the present invention has the combined advantages of providing for stable storage of IGF-I solutions with IGF-I concentrations greater than 12 mg/ml and pH values greater than pH 5.5 for extended periods of time.

IGF-I and analogues thereof, for use in the subject compositions, can be produced in any number of ways which are well known in the art. For example, the IGF-I polypeptides can be isolated directly from blood, such as from serum or plasma, by known methods. See, e.g., U.S. Patent No. 4,769,361; Svoboda et al., *Biochemistry* (1980) 19:790–797; Cornell and Boughdady, *Prep. Biochem.* (1982) 12:57; and Cornell and Boughdady, *Prep. Biochem.* (1984) 14:123. Alternatively, IGF-I can be synthesized chemically, by any of several techniques that are known to those skilled in the peptide art. See, e.g., Stewart and Young, *Solid Phase Peptide Synthesis* (Pierce Chemical Co., Rockford, Ill., 1984) and Barany and Merrifield, *The Peptides: Analysis,*

Synthesis, Biology, ed. Gross and Meienhofer, Vol. 2 (Academic Press, New York, 1980), pp. 3–254, for solid phase peptide synthesis techniques; and Bodansky, *Principles of Peptide Synthesis* (Springer-Verlag, Berlin, 1984); and Gross and Meienhofer, eds., *The Peptides: Analysis, Synthesis, Biology*, Vol. 1 (Academic Press, New York, 1980), for classical solution synthesis. The IGF-I polypeptides of the present invention can also be chemically prepared by the method of simultaneous multiple peptide synthesis. See, e.g., Houghten, *Proc. Natl. Acad. Sci.* USA (1985) 82:5131–5135; U.S. Patent No. 4,631,211.

Alternatively and preferably, the IGF-I polypeptides can be obtained using recombinant methods. In this regard, the recombinant production of IGF-I in bacterial and yeast hosts and purification therefrom has been described. See, e.g., International Publication Nos. WO 96/40776, WO 96/07744, WO 95/06059, WO 95/06064, WO 95/16777, WO 93/11240, and WO 92/04363; EP 567,554 B; U.S. Pat. Nos. 5,650,496, 5,612,198, 5,407,810, 5,410,026, 5,288,931, 5,324,639, and 5,231,178; Chang and Swartz, *Protein Folding: In Vivo and In Vitro* (American Chemical Society, 1993), pp. 178–188; Elliott et al., *J Protein Chem.* (1990) 9:95–104.

For example, IGF-I can be produced in methyl as in a protease deficient *Pichia pastoris* strain, as well as in *Saccharomyces cerevisiae* (see, e.g., U.S. Pat. Nos. 5,231, 178, 5,324,639, 5,612,198, and 5,650,496; International Publication Nos. WO 96/40776, WO 96/07744, and WO 92/04363; and EP 567,554 B; all of which are herein incorporated by reference.

The IGF-I will either be secreted, if appropriate leader sequences are used, or produced intracellularly and the cells manipulated to allow proper isolation of an IGF-containing product. Particularly preferred methods for producing IGF-I, e.g., in yeast, generally utilize a secretion leader, such as a leader sequence derived from the yeast α-factor signal sequence, as described in EP 128,733. Production in yeast generally includes a fermentation step for cell amplification, followed by purification and refolding to obtain an authentic, properly folded protein. Methods for fermenting the culture, purification, and refolding are well known in the art. See, e.g., U.S. Pat. Nos. 5,324,639 and 5,650,496, and International Publication Nos. WO 96/07744 and WO 96/40776, herein incorporated by reference.

Once obtained, IGF-I is formulated with one or more solubilizing compounds that include a guanidinium group, in order to enhance the solubility of IGF-I at pH 5.5 or greater, to provide a composition including IGF-I at a concentration of 12 mg/ml or higher that can be stored at 4° C. Alternatively, concentrated forms of IGF-I, such as freeze-dried formulations, can be reconstituted or diluted with a solution containing a compound having a guanidinium group to provide a concentration of IGF-I above 12 mg/ml and a solution with a pH above pH 5.5.

Suitable solubilizing compounds include, without limitation, arginine, arginine analogues, guanidine-containing compounds such as guanidine, guanidine acetate, guanidine amine, guanidine carbonate, guanidine 1-cyano, guanidine 1,3-diphenyl, guanidine 1,3-di(2-toyl), guanidine hydrochloride, guanidine nitrate, 1-nitroguanidine, guanidine picrate, guanidine thiocyanate, guanidine tetraphenyl, guanidine 1,1,3-triphenyl, guanidine 1,2,3-triphenyl, guanidine 1-ureido, agmatine, 4-guanidinobenzoic acid, guanidoacetic acid, guanidinosuccinic acid, guanethidine, 4'acetamidophenyl 4-guanidinobenzoate, 2-iminobiotin, N-(2-guanidinoethyl)-5-isoquinolinesulfonamide, guaninobutyric acid, guanidinopropionic acid, and the like, commercially available from, e.g., Sigma Chemical Company, St. Louis, Mo. Of these compounds, arginine, guanidine hydrochloride, agmatine, 4-guanidinobenzoic acid, guanidoacetic acid, and guanidinosuccinic acid, are preferred.

In most cases, concentrations of the solubilizing compound will affect the achievable concentration of the IGF-I, such that, for example, the greater the concentration of the solubilizing compound, the greater the maximum concentration of IGF-I possible. The temperature of the IGF-I composition will also have an effect on the solubility of the IGF-I, such that a higher temperature will increase the solubility of the IGF-I. Thus, the amount of solubilizing compound present will depend on the nature of the guanidinium group compound, its solubility, its effect on solubility of IGF-I, the desired concentration of IGF-I to be achieved in the composition, and the temperature at which the composition will be maintained. The optimum concentration for each solubilizing compound may differ but is readily determined by one of skill in the art.

In general, the concentration of the solubilizing compound present in the composition will be from about 10 mM to about 1 M, preferably about 15 mM to about 500 mM, and more preferably, for example, in the case of the compound arginine, in a concentration range of about 20 mM to about 200 mM. At 200 mM arginine, for example, the concentration of IGF-I can be as high as about 200 mg/ml or more.

The IGF-I compositions of the present invention may also include buffers that maintain a pH above pH 5.5, up to a pH of about 9.0, more preferably, up to a pH of about 7.5. The preferred pH of the composition, with or without a buffer, is in a range from about pH 5.7 to about pH 6.3, and preferably about pH 6.0. Because of the presence of one or more of the solubilizing agents discussed above, the achievable concentration of IGF-I is higher than previously possible at pH 5.5, and hence the compositions of the present invention provide a concentration of IGF-I suitable and optimal for therapeutic usage.

The buffer used to achieve the pH of the IGF-I composition can be any acceptable buffer capable of maintaining the pH in the desired range upon addition of acid or alkali and which is not biologically or otherwise undesirable, i.e., the buffer does not cause undesirable biological effects and does not interact in a deleterious manner with any of the other components of the composition. For example, where the composition will be administered to a human, the buffer should be nontoxic to humans (at least nontoxic at the dosages used). Suitable buffers include, but are not limited to, phosphoric acid buffers, carbonic acid buffers, including for example, glutaric acid, maleic acid, succinic acid, citric acid, imidazole, or histidine, in concentrations suitable to achieve the desired pH, e.g., in the range of 5 to 50 mM.

If the composition is freeze-dried or concentrated, reconstitution of the composition can be achieved using a buffer as described above, so that the composition is of the desired pH. Additionally, the buffer components can also be freeze-dried or concentrated and upon reconstitution, provide the desired pH for the composition.

In addition to the maintenance of an acceptable and desirable pH, where the IGF-I composition is used for delivery to a mammal such as a human, the isotonicity of the composition is also a consideration. Thus, the preferred composition for an injectable solution of IGF-I will provide an isotonicity the same as, or similar to, that of patient serum or body fluids. To achieve the isotonicity, a salt such as sodium chloride, potassium chloride, a phosphate buffer, dextrose, or sucrose, can be added to the solution, at an appropriate concentration. For example, if sodium chloride is used, about a 150 mM sodium chloride solution will provide adequate isotonicity. Isotonicity may also be provided, in part, by the guanidinium-containing compound, for example, to provide a solution with a final salt concentration of about 150 mM.

Another advantage of the composition of the invention is its capability for stable long-term storage, such that IGF-I activity is preserved. Generally, the composition will be stored in solution within the range of about 2° C. to about 40° C., more preferably at refrigerated temperatures, e.g., from about 2° C. to about 8° C., and most preferably at about 4° C., so that the IGF-I solution remains stable and safe for eventual administration to a patient. If the IGF-I is prepared in a freeze-dried composition, it can be stored at room temperature and reconstituted for immediate use or for storage at refrigerated temperatures for future use. At refrigerated temperatures and at a pH of about pH 6.0, the IGF-I composition of the invention is stable for at least 6 months.

The concentration of IGF-I achievable by the compositions of the invention includes a concentration of IGF-I greater than about 12 mg/ml up to about 200 mg/ml, preferably greater than about 15 mg/ml, more preferably greater than about 20 mg/ml, even more preferably greater than about 25 mg/ml, and most preferably greater than about 50 mg/ml to about 200 mg/ml. As explained above, the concentration of IGF-I achievable will depend on the concentration of the solubilizing compound, and also to some extent, on the isotonic character of the solution, the pH, and the temperature of the solution. One of skill in the art can determine appropriate concentrations of IGF-I for given uses and readily prepare IGF-I compositions with any desired IGF-I concentration within this range.

The IGF-I compositions of the present invention are generally formulated with a pharmaceutically acceptable excipient or vehicle, including liquids such as water or saline. Suitable excipients for nonliquid formulations are also known to those of skill in the art. Additionally, auxiliary substances, such as wetting or emulsifying agents, pH buffering substances, surfactants, and the like, may be present in such vehicles.

The compositions may also include carriers. Suitable carriers may be large, gel or foam-like compositions, slowly metabolized macromolecules such as proteins, polysaccharides, polylactic acids, polyglycolic acids, polymeric amino acids, amino acid copolymers, poly(ethylene glycol) or PEG, hydrogels, and inactive virus particles. Such carriers are well known to those of ordinary skill in the art. Liposomes may also be used as carriers, such as, for example, the liposome compositions described in U.S. Pat. No. 5,422,120, International Publication Nos. WO 95/13796, WO 94/23697, and WO 91/14445, and EP 524,968 B1.

Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's *Pharmaceutical Sciences* (Mack Pub. Co., New Jersey, 1991).

Typically, the compositions are prepared as injectables, either as liquid solutions or suspensions. Solid forms suitable for solution in, or suspension in, liquid vehicles prior to injection, may also be prepared. The IGF-I compositions may also be formulated in an implant or in a sustained release formulation. Liposomes carriers or other gel components, for example, may be used to facilitate this means of administration.

A pharmaceutically or therapeutically effective amount of IGF-I will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present invention, generally a therapeutic amount of an IGF-I composition will be in the range of about 0.1 µg/kg to about 100 mg/kg, more preferably about 1 µg/kg to about 1 mg/kg, and most preferably about 2 µg/kg to about 100 µg/kg, in at least one dose. The subject may be administered as many doses as is required to reduce and/or alleviate the signs, symptoms, or causes of the disorder in question, or bring about any other desired alteration of a biological system.

Administration of the formulated IGF-I polypeptide is generally accomplished parenterally. Parenteral administration can include, for example, administration intravenously, intra-arterially, intra-articularly, subcutaneously, intradermally, intramuscularly, intranasally, mucosally, and by aerosol administration. For example, the composition can be administered by inhalation, e.g., as a nasal or mouth spray or aerosol. Administration of the composition of the invention can be accomplished by, for example, injection, catheterization, laser-created perfusion channels, a particle gun, and a pump.

Once formulated, the IGF-I compositions can be used for a variety of purposes. In this regard, the IGF-I compositions can be used, e.g., to stimulate growth of cells in vitro or in vivo in a variety of tissues and cell types. The compositions can also be used for bone repair and replacement therapy, to treat osteoporosis, to inhibit an inflammatory response, ischemic injury, and organ rejection upon transplantation, and to increase lactation and meat production in cattle and other farm animals. Additionally, IGF-I can be combined with the solubilizing agent during purification procedures to enhance yields.

Below are examples of specific embodiments for carrying out the present invention. The examples are offered for illustrative purposes only and are not intended to limit the scope of the present invention in any way.

EXPERIMENTAL

IGF-I for use in these experiments was recombinantly produced in the yeast strain *Pichia pastoris* and purified essentially as described in U.S. Pat. Nos. 5,324,639, 5,324,660, 5,650,496 and International Publication No. WO 96/40776.

Example 1

Solubility of Various IGF-I Preparations

Following isolation, recombinant human IGF-I (rhIGF-I) was formulated with the various excipients listed in Table 1 and solubility determined at room temperature and at 4° C. by dialysis. In particular, a concentrated solution of rhIGF-I (20 mg/ml at pH 4.0) was dialyzed against each of the buffers listed in Table 1 using 3000 dalton molecular weight cutoff tubing and three 20-fold volume changes. After buffer exchange was complete, the rhIGF-I formed two distinct phases, a layer of insoluble (precipitated) rhIGF-I and a solution phase containing a saturated solution of rhIGF-I. A sample of the solution phase rhIGF-I was taken and filtered through a 0.22 mm filter to remove insoluble material. The concentration of the filtered rhIGF-I solution was determined by UV spectroscopy using the known rhIGF-I absorption coefficient, i.e., 0.62 absorbance units at 277 nm for a 1 mg/ml solution. Those that showed enhanced solubility were then tested at 4° C.

As can be seen, in the presence of almost all of the substances tested, rhIGF-I solubility is significantly reduced at 4° C. as compared to room temperature. However, arginine significantly enhanced the solubility of rhIGF-I both at room temperature and at 4° C. Since the experiments reported in Table 1 were run using 20 mg/ml rhIGF-I, values in Table 1 below 20 mg/ml represent the maximum solubility for that particular formulation. Arginine remains soluble at about 20 mg/ml. Thus, the maximum solubility of rhIGF-I in an arginine-containing formulation is above about 20 mg/ml. This is also true for histidine-containing compositions at room temperature but not at 4° C.

TABLE 1

Concentration of rhIGF-I in Various Formulations

| Formulation (pH 6.0) | [rhIGF-I] (mg/ml) @ R.T. | [rhIGF-I] (mg/ml) @ 4° C. |
| --- | --- | --- |
| 10 mM Na Citrate | 5.2 | 3.4 |
| 10 mM Na Citrate, 50 mM NaCl | 8.7 | 5.6 |
| 10 mM Na Citrate, 100 mM NaCl | 10.4 | 7.9 |
| 10 mM Na Citrate, 150 mM NaCl | 16.9 | 9.9 |
| 10 mM Na Citrate, 250 mM NaCl | 15.2 | 9.6 |
| 10 mM Na Citrate, 500 mM NaCl | 11.7 | 7.6 |
| 10 mM Na Citrate, 5% Sucrose | 7.0 | |
| 10 mM Na Citrate, 10% Sucrose | 9.0 | |
| 10 mM Na Citrate, 20% Sucrose | 13.2 | |
| 10 mM Na Citrate, 150 mM NaCl, 0.01% Tween 80 | 16.0 | 10.3 |
| 10 mM Na Citrate, 150 mM NaCl, 0.2% Pluronic F68 | 16.4 | 10.2 |
| 10 mM Na Citrate, 140 mM NaCl, 10 mM MgCl2 | 17.4 | 10.9 |
| 10 mM Na Citrate, 140 mM NaCl, 10 mM ZnCl2 | 14.4 | 8.4 |
| 10 mM Na Citrate, 100 mM Alanine | 5.0 | |
| 10 mM Na Citrate, 100 mM Valine | 5.2 | |
| 10 mM Na Citrate, 100 mM Leucine | 6.4 | |
| 10 mM Na Citrate, 100 mM Isoleucine | 6.4 | |
| 10 mM Na Citrate, 100 mM Methionine | 7.3 | |
| 10 mM Na Citrate, 100 mM Proline | 5.8 | |
| 10 mM Na Citrate, 100 mM Serine | 5.2 | |
| 10 mM Na Citrate, 100 mM Threonine | 4.9 | |
| 10 mM Na Citrate, 100 mM Asparagine | 6.0 | |
| 10 mM Na Citrate, 100 mM Glutamine | 6.3 | |
| 10 mM Na Citrate, 100 mM Cysteine | 0.8 | |
| 10 mM Na Citrate, 100 mM Glycine | 5.6 | 4.0 |
| 10 mM Na Citrate, 100 mM Lysine | 15.5 | 9.9 |
| 10 mM Na Citrate, 100 mM Arginine | 20.9 | 19.7 |
| 10 mM Na Citrate, 100 mM Histidine | 20.5 | 5.8 |

Example 2

Effect of Arginine on IGF-I Solubility

In order to further test the effect of arginine concentration on the solubility of IGF-I at 4° C., pH 6.0, a concentrated solution of rhIGF-I (50–200 mg/ml, pH 4.0) was dialyzed against buffers containing between 0 and 115 mM arginine, using 3000 dalton molecular weight cutoff tubing and three 20-fold volume changes. After buffer exchange was complete, the rhIGF-I formed two distinct phases, a layer of insoluble (precipitated) rhIGF-I and a solution phase containing a saturated solution of rhIGF-I. A sample of the solution phase rhIGF-I was taken and filtered through a 0.22 µm filter to remove insoluble material. The concentration of the filtered rhGF-I solution was determined by UV spectroscopy using the known IGF-I absorption coefficient, i.e., 0.62 absorbance units at 277 nm for a 1 mg/ml solution.

Figure 2:
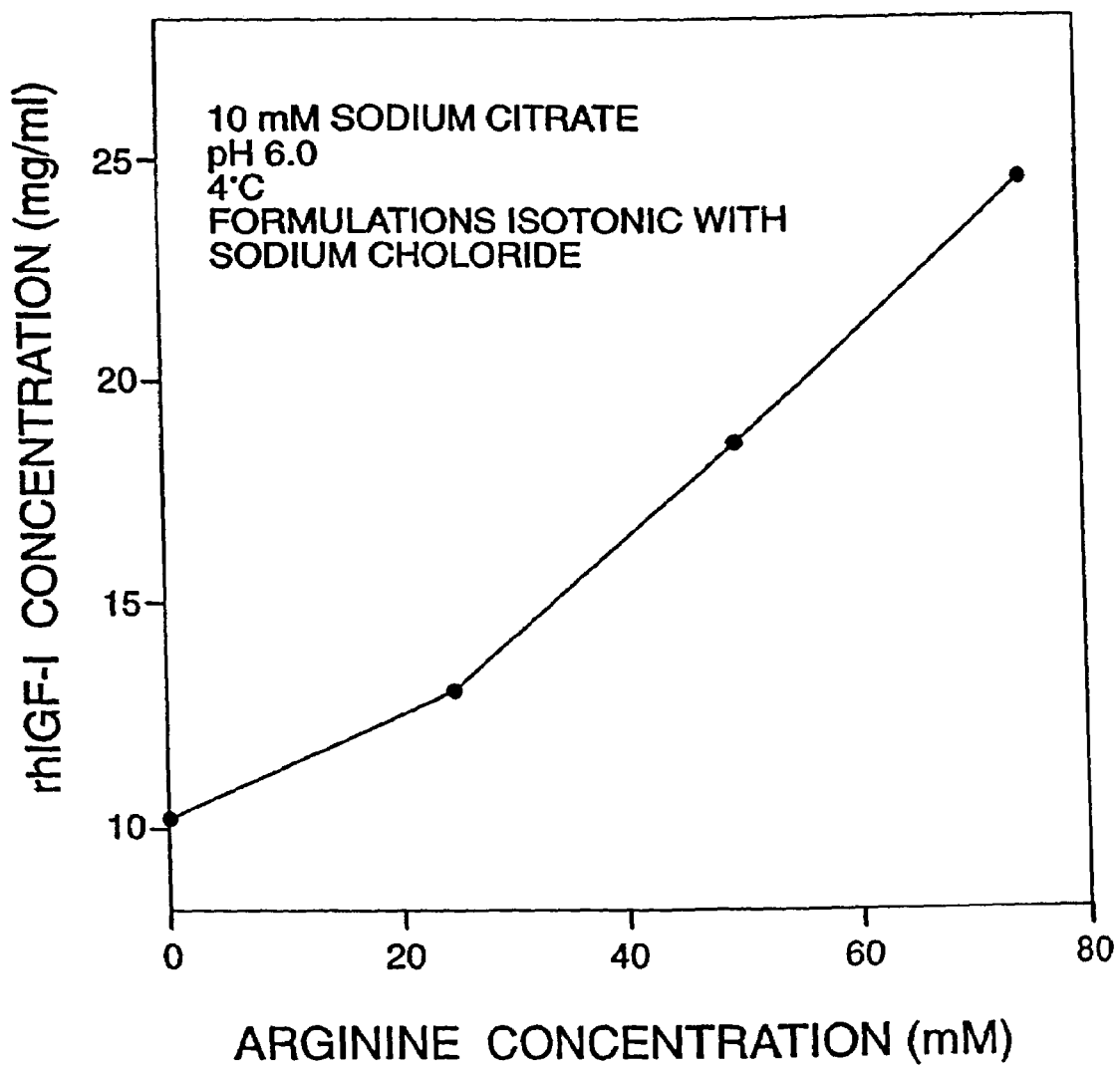
FIG. 2 shows rhIGF-I solubility as a function of arginine concentration in a 10 mM sodium citrate buffer and made isotonic with sodium chloride, pH 6.0, at 4° C.

As can be seen in FIGS. 1 and 2, as the concentration of arginine increased, so did the solubility of rhIGF-I.

Example 3

Effect of Guanidinium Group on IGF-I Solubility

To test whether the presence of a guanidinium group on arginine was responsible for the increase in rhIGF-I solubility, the effect of arginine and several compounds of similar structure were tested for their ability to solubilize rhIGF-I. Arginine, N-acetyl-arginine, guanidine hydrochloride, lysine, glycine, ornithine, and citrulline were examined up to a concentration of 200 mM in pH 6.0 formulations. To measure the concentration of rhIGF-I, a concentrated solution of rhIGF-I (>100 mg/ml, pH 4.0) was dialyzed against buffers containing between 0 and 200 mM of each compound, using 3500 dalton molecular weight cutoff tubing and three 20-fold volume changes. After buffer exchange was complete, the rhIGF-I formed two distinct phases, a layer of insoluble (precipitated) rhIGF-I and a solution phase containing a saturated solution of rhIGF-I. A sample of the solution phase rhIGF-I was taken and filtered through a 0.22 µm filter to remove insoluble material. The concentration of the filtered rhIGF-I solution was determined by UV spectroscopy using the known rhIGF-I absorption coefficient, i.e., 0.62 absorbance units at 277 nm for a 1 mg/ml solution.

Figure 3:
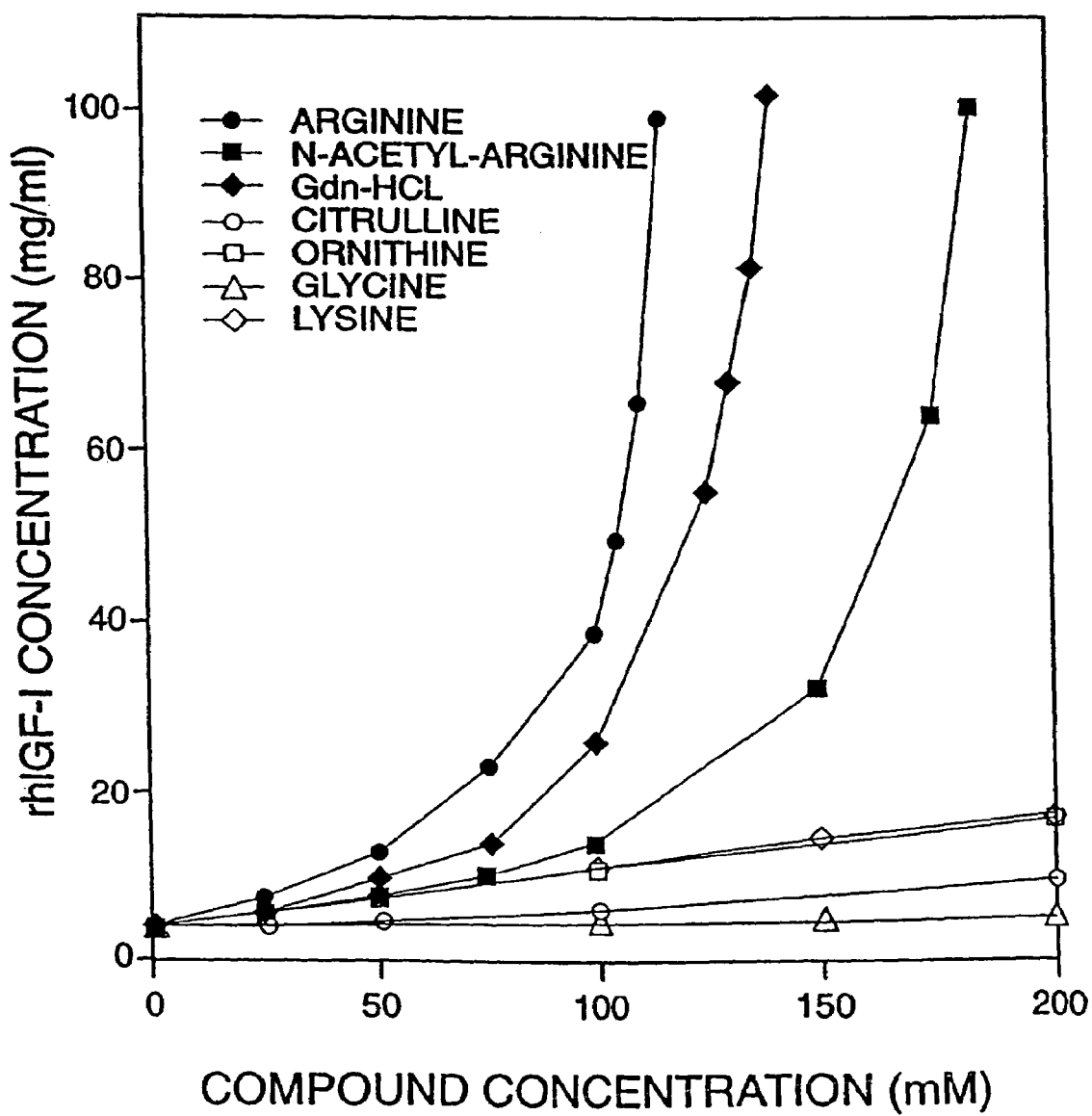
FIG. 3 shows rhIGF-I solubility as a function of the concentration of arginine or one of several other compounds of similar structure, some of which contain a guanidinium group and some of which do not.

As can be seen in FIG. 3, the presence of compounds containing a guanidinium group (arginine, N-acetyl-arginine, and guanidine hydrochloride) greatly solubilized rhIGF-I, while compounds similar in structure, but containing no guanidinium group (glycine, lysine, ornithine, citrulline), did not.

Example 4

Effect of pH on IGF-I Solubility

In order to test the effects of pH on IGF-I solubility in the absence of a guanidinium-containing compound, IGF-I compositions containing rhIGF-I at varying concentrations, in 20 mM sodium citrate, 20 mM sodium phosphate, 90 mM sodium chloride, at 4° C. and at varying pHs were used. In particular, a concentrated solution of rhIGF-I (50–200 mg/ml, pH 4.0) was dialyzed against buffers containing 20 mM sodium citrate, 20 mM sodium phosphate, 90 mM sodium chloride, between pH 3.0 and 8.0, as described above. After buffer exchange was complete, the rhIGF-I formed two distinct phases, a layer of insoluble (precipitated) rhIGF-I and a solution phase containing a saturated solution of rhIGF-I. A sample of the solution phase rhIGF-I was taken and filtered through a 0.22 µm filter to remove insoluble material. The concentration of the filtered rhIGF-I solution was determined by UV spectroscopy using the known IGF-I absorption coefficient, i.e., 0.62 absorbance units at 277 nm for a 1 mg/ml solution.

Figure 4:
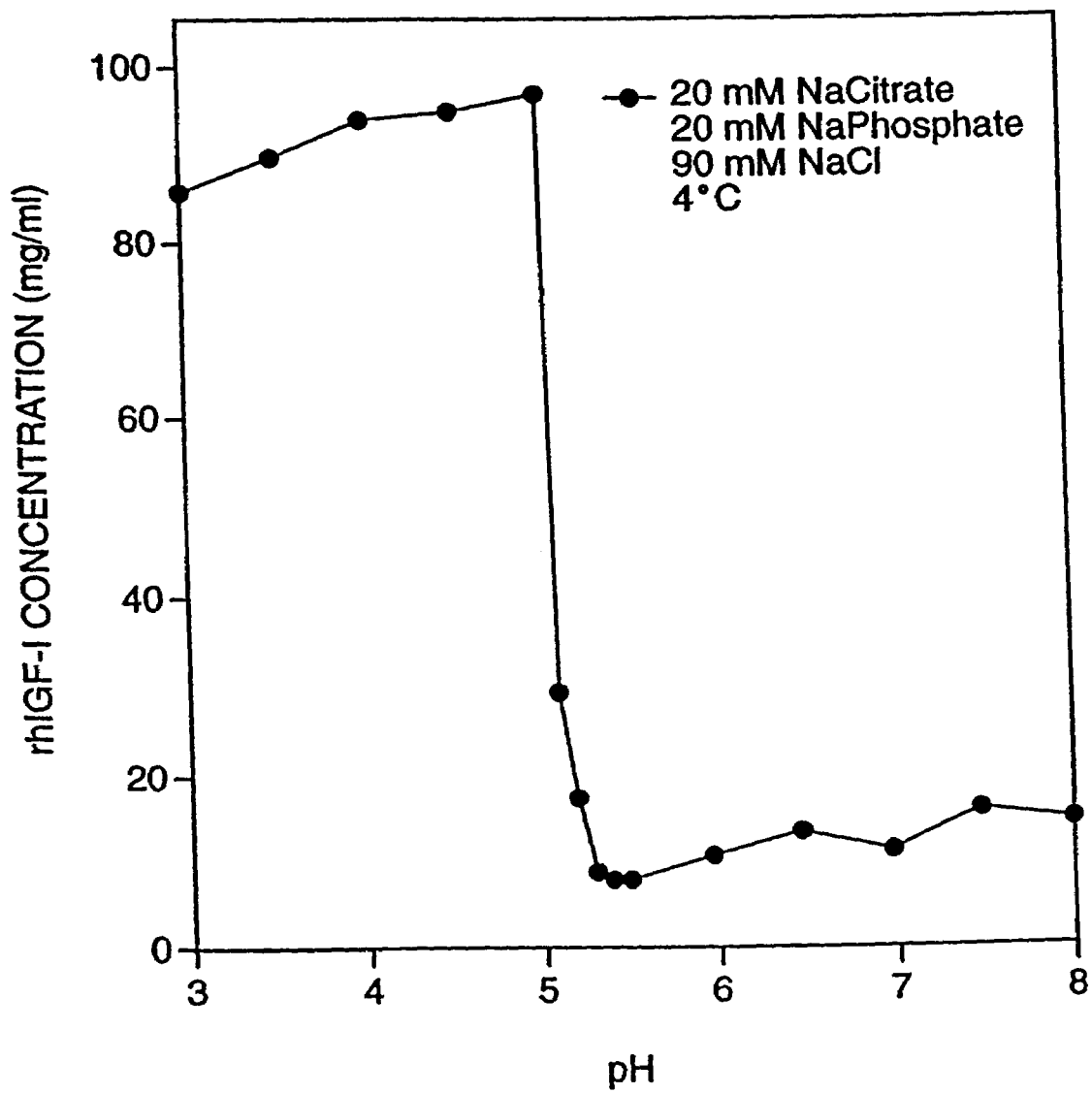
FIG. 4 shows rhIGF-I solubility in a citrate/phosphate buffer made isotonic with sodium chloride, as a function of pH.

As shown in FIG. 4, pH had a large impact on rhIGF-I solubility. About a 10-fold reduction in solubility was seen when the pH increased from pH 5.0 to pH 5.5. At pH 5.5, rhIGF-I was only soluble to 9–10 mg/ml in an isotonic composition at 4° C. However, as shown in Examples 1–3 and FIGS. 1–3, in the presence of a guanidinium-containing compound such as arginine or guanidine hydrochloride, concentrations of rhIGF-I well above this value remained soluble.

Example 5

Formulation of IGF-I with Arginine for Injection

Purified, rhIGF-I prepared as described in Example 1, was formulated with arginine using dialysis or diafiltration as follows.

By dialysis, bulk rhIGF-I was placed in dialysis tubing with a molecular weight cutoff of 1000 to 3000 daltons and dialyzed against three 20-fold volume changes of formulation buffer containing arginine at a concentration of 50 mM, 10 mM sodium citrate, and 90 mM sodium chloride, pH 6.0. Each 20-fold volume change was dialyzed for not less than 3 hours and preferably more than 12 hours. Dialysis was done at 4° C. or at room temperature.

By diafiltration, bulk rhIGF-I was diafiltered against 10 volumes of formulation buffer containing arginine using a membrane with a molecular weight cutoff of 1000 to 3000 daltons, and diafiltered against three 20-fold volume changes of formulation buffer containing arginine at a concentration of 50 mM, 10 mM sodium citrate, and 90 mM sodium chloride. Diafiltration was performed at 4° C. or at room temperature.

The resulting compositions contained rhIGF-I at a concentration of about 12 mg/ml.

Example 6

Stability of rhIGF-I Formulated with Arginine

The rhIGF-I composition from Example 5 was stored refrigerated at 2° C. to 8° C. in type I glass vials for 6 months. Stability analysis of rhIGF-I was accomplished by reverse-phase HPLC and SDS-PAGE. Additionally, the bioactivity of rhIGF-I was assessed by a cell proliferation assay. These assays indicated that the rhIGF-I was fully active after 6 months at 2° C. to 8° C. and contained no detectable degradation of rhIGF-I as compared to a control aliquot of rhIGF-I.

Example 7

Effect of Arginine on Solubility of IGF-I with Freeze-Thaw

When an aqueous solution is frozen, water crystallizes to ice and all solutes between the ice crystals are concentrated. Thus, during freezing, IGF-I may be concentrated beyond its solubility, resulting in precipitation of IGF-I. Upon thawing, the precipitated IGF-I may not completely return to solution, resulting in a solution of decreased IGF-I concentration. It is desirable to have a pharmaceutical composition of IGF-I that can be frozen and thawed multiple times with no loss in concentration.

Figure 5:
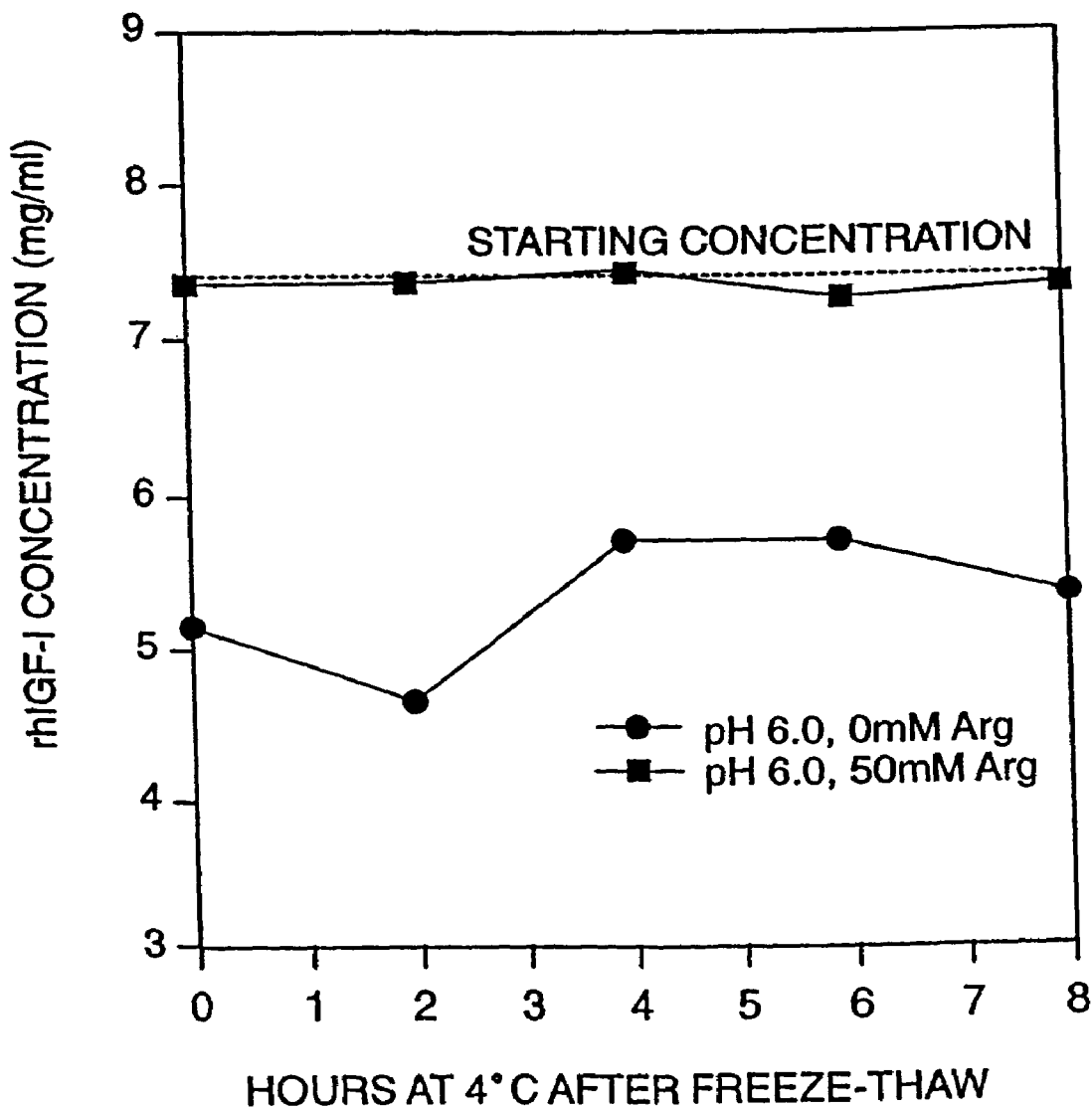
FIG. 5 shows effect of arginine (0 mM or 50 mM) in solution on solubility of rhIGF-I (initial concentration of 7.4 mg/ml) following freeze-thaw between −20° C. to 4° C.

The effect of arginine on IGF-I solubility with freeze-thaw between −20° C. and 4° C. was determined. Isotonic formulations at pH 6.0 containing 7.4 mg/ml rhIGF-I, 10 mM sodium citrate, and either 0 mM arginine or 50 mM arginine were tested. As can be seen in FIG. 5, the addition of arginine to the solution stabilized rhIGF-I solubility and prevented a loss of rhIGF-I concentration following freeze-thaw between −20° C. and 4° C.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A composition having a pH of about pH 5.5 or greater, wherein said composition comprises:
    (a) biologically active insulin-like growth factor-1 (IGF-I) or biologically active analogue thereof having an amino acid sequence that shares at least 70% sequence identity with the amino acid sequence for human IGF-I, wherein said IGF-I or analogue thereof is present at a concentration of about 12 mg/ml to about 200 mg/ml when said composition is at a temperature of about 4° C.; and
    (b) a solubilizing compound selected from the group consisting of guanidine, guanidine acetate, guanidine carbonate, guanidine 1-cyano, guanidine 1,3-diphenyl, guanidine 1,3-di(2-toyl), guanidine hydrochloride, guanidine nitrate, 1-nitroguanidine, guanidine picrate, guanidine thiocyanate, guanidine tetraphenyl, guanidine 1,1,3-triphenyl, guanidine 1,2,3-triphenyl, agmatine, 4-guanidinobenzoic acid, guanidinoacetic acid, guanidinosuccinic acid, guanethidine, 4'-acetamidophenyl 4-guanidinobenzoate, 2-iminobiotin, N-(2-guanidinoethyl)-5-isoquinolinesulfonamide, guanidinobutyric acid, and guanidinopropionic acid, wherein said solubilizing compound is present in said composition in an amount sufficient to make said IGF-I or analogue thereof soluble at a concentration of about 12 mg/ml to about 200 mg/ml when said composition is at a temperature of about 4° C.

2. The composition of claim 1, wherein said IGF-I or analogue thereof has an amino acid sequence having at least 95% sequence identity with the amino acid sequence for human IGF-I.

3. The composition of claim 1, wherein said IGF-I is human IGF-I.

4. The composition of claim 1, wherein said pH is in a range from about pH 5.5 to about pH 9.0.

5. The composition of claim 4, wherein said pH is in a range from about pH 5.7 to about pH 6.3.

6. The composition of claim 5, wherein said pH is about pH 6.0.

7. The composition of claim 1, wherein said composition comprises sodium chloride at a molar concentration of about 150 mM.

8. The composition of claim 1 comprising a buffer selected from the group consisting of a glutaric acid buffer, a maleic acid buffer, a succinic acid buffer, a citric acid buffer, imidazole, and a histidine buffer.

9. A composition comprising:
    (a) biologically active insulin-like growth factor-1 (IGF-I) or biologically active analogue thereof having an amino acid sequence that shares at least 70% sequence identity with the amino acid sequence for human IGF-I, wherein said IGF-I or analogue thereof is present at a concentration of about 12 mg/ml to about 200 mg/ml when said composition is at a temperature of about 4° C.;
(b) a solubilizing compound selected from the group consisting of guanidine, guanidine acetate, guanidine carbonate, guanidine 1-cyano, guanidine 1,3-diphenyl, guanidine 1,3-di(2-toyl), guanidine hydrochloride, guanidine nitrate, 1-nitroguanidine, guanidine picrate, guanidine thiocyanate, guanidine tetraphenyl, guanidine 1,1,3-triphenyl, guanidine 1,2,3-triphenyl, agmatine, 4-guanidinobenzoic acid, guanidinoacetic acid, guanidinosuccinic acid, guanethidine, 4'-acetamidophenyl 4-guanidinobenzoate, 2-iminobiotin, N-(2-guanidinoethyl)-5-isoquinolinesulfonamide, guanidinobutyric acid, and guanidinopropionic acid, wherein said solubilizing compound is present in said composition in an amount sufficient to make said IGF-I or analogue thereof soluble at a concentration of about 12 mg/ml to about 200 mg/ml when said composition is at a temperature of about 4° C.; and
(c) a buffer such that the composition has a pH of about pH 5.5 to about pH 9.0.

10. The composition of claim 9, wherein said IGF-I or analogue thereof has an amino acid sequence having at least 95% sequence identity with the amino acid sequence for human IGF-I.

11. The composition of claim 9, further comprising sodium chloride at a molar concentration of about 150 mM.

12. A composition having a pH of about pH 5.5 or greater, wherein said composition comprises:
(a) biologically active human insulin-like growth factor-1 (IGF-I), wherein said IGF-I is present at a concentration of about 12 mg/ml to about 200 mg/ml when said composition is at a temperature of about 4° C.; and
(b) a solubilizing compound selected from the group consisting of guanidine, guanidine acetate, guanidine carbonate, guanidine 1-cyano, guanidine 1,3-diphenyl, guanidine 1,3-di(2-toyl), guanidine hydrochloride, guanidine nitrate, 1-nitroguanidine, guanidine picrate, guanidine thiocyanate, guanidine tetraphenyl, guanidine 1,1,3-triphenyl, guanidine 1,2,3-triphenyl, agmatine, 4-guanidinobenzoic acid, guanidinoacetic acid, guanidinosuccinic acid, guanethidine, 4'-acetamidophenyl 4-guanidinobenzoate, 2-iminobiotin, N-(2-guanidinoethyl)-5-isoquinolinesulfonamide, guanidinobutyric acid, and guanidinopropionic acid, wherein said solubilizing compound is present in said composition in an amount sufficient to make said IGF-I soluble at a concentration of about 12 mg/ml to about 200 mg/ml when said composition is at a temperature of about 4° C.

13. The composition of claim 12, wherein said pH is in a range from about pH 5.5 to about pH 9.0.

14. The composition of claim 13, wherein said pH is in a range from about pH 5.7 to about pH 6.3.

15. The composition of claim 14, wherein said pH is about pH 6.0.

16. The composition of claim 12, wherein said composition comprises sodium chloride at a molar concentration of about 150 mM.

17. The composition of claim 12 comprising a buffer selected from the group consisting of a glutaric acid buffer, a maleic acid buffer, a succinic acid buffer, a citric acid buffer, imidazole, and a histidine buffer.

18. A composition comprising:
(a) biologically active human insulin-like growth factor-1 (IGF-I), wherein said IGF-I is present at a concentration of about 12 mg/ml to about 200 mg/ml when said composition is at a temperature of about 4° C.;
(b) a solubilizing compound selected from the group consisting of guanidine, guanidine acetate, guanidine carbonate, guanidine 1-cyano, guanidine 1,3-diphenyl, guanidine 1,3-di(2-toyl), guanidine hydrochloride, guanidine nitrate, 1-nitroguanidine, guanidine picrate, guanidine thiocyanate, guanidine tetraphenyl, guanidine 1,1,3-triphenyl, guanidine 1,2,3-triphenyl, agmatine, 4-guanidinobenzoic acid, guanidinoacetic acid, guanidinosuccinic acid, guanethidine, 4'-acetamidophenyl 4-guanidinobenzoate, 2-iminobiotin, N-(2-guanidinoethyl)-5-isoquinolinesulfonamide, guanidinobutyric acid, and guanidinopropionic acid, wherein said solubilizing compound is present in said composition in an amount sufficient to make said IGF-I soluble at a concentration of about 12 mg/ml to about 200 mg/ml when said composition is at a temperature of about 4° C.; and
(c) a buffer such that the composition has a pH of about pH 5.5 to about pH 9.0.

19. The composition of claim 18, further comprising sodium chloride at a molar concentration of about 150 mM.

* * * * *